US012805730B2

(12) United States Patent
Chieh

(10) Patent No.: US 12,805,730 B2
(45) Date of Patent: Nov. 24, 2026

(54) DENTAL PHOTOGRAPHY OR DETECTION DEVICE AND SYSTEM

(71) Applicant: National Taiwan Normal University, Taipei City (TW)

(72) Inventor: Jen-Jie Chieh, Taoyuan City (TW)

(73) Assignee: NATIONAL TAIWAN NORMAL UNIVERSITY, Taipei City (TW)

( * ) Notice: Subject to any disclaimer, the term of this patent is extended or adjusted under 35 U.S.C. 154(b) by 59 days.

(21) Appl. No.: 19/028,005

(22) Filed: Jan. 17, 2025

(65) Prior Publication Data

US 2025/0241536 A1 Jul. 31, 2025

(30) Foreign Application Priority Data

Jan. 31, 2024 (TW) ................................ 113103716

(51) Int. Cl.
*A61B 5/00* (2006.01)

(52) U.S. Cl.
CPC .......... *A61B 5/0088* (2013.01); *A61B 5/0022* (2013.01); *A61B 5/0075* (2013.01)

(58) Field of Classification Search
CPC ... A61B 5/0013; A61B 5/0022; A61B 5/0075; A61B 5/0088; A61B 5/7264
See application file for complete search history.

(56) References Cited

U.S. PATENT DOCUMENTS

| | | | | |
|---|---|---|---|---|
| 2017/0215997 A1* | 8/2017 | Martin | ................. | A61B 5/6835 |
| 2023/0148269 A1* | 5/2023 | Kim | ....................... | A61B 5/442 600/306 |

FOREIGN PATENT DOCUMENTS

| | | |
|---|---|---|
| CN | 105358092 A | 2/2016 |
| CN | 109124576 A | 1/2019 |
| TW | M657793 U | 7/2024 |

* cited by examiner

*Primary Examiner* — Hina F Ayub
(74) *Attorney, Agent, or Firm* — MUNCY, GEISSLER, OLDS & LOWE, P.C.

(57) ABSTRACT

A dental photography or detection device, for obtaining multiple detection images from reflection of or excitation by multiple different light sources illuminating on teeth and gums mainly by means of multiple different filters of multiple multiphoton lens modules, and sensing multiple reflection or excitation lights of the teeth and the gums by using optical characteristic measurement. Subsequently, an integrated circuit or cloud server analyzes and processes the reflected or excited detection images or lights of the teeth and the gums, so as to obtain dental plaque distribution, dental calculus distribution and subgingival calculus distribution of corresponding teeth. In addition, the dental photography or detection device is configured with a rotation motor for controlling the multiphoton lens modules to rotate, so as to obtain dental detection images of different teeth, and the integrated circuit or cloud server can synthesize multiple dental detection images into a panoramic dental detection image.

9 Claims, 6 Drawing Sheets

DENTAL PHOTOGRAPHY OR DETECTION DEVICE AND SYSTEM

BACKGROUND OF THE INVENTION a) Field of the Invention

The present invention relates to a dental photography or detection device and system, and more particularly to a dental photography or detection device and system having a multiphoton lens module, an optical characteristic measurement module and a rotation motor, and capable of obtaining dental plaque distribution, dental calculus distribution and subgingival calculus distribution of corresponding teeth according to an acquired dental detection image.

b) Description of the Prior Art

Dental cleaning is an essential hygiene practice for everyone, poor dental cleaning leads to increased dental plaque accumulation on teeth, and the accumulated dental plaque forms dental calculus on teeth surface or subgingival calculus which is located out of the teeth surface. The traditional method of detecting dental plaque is by coating an enzyme on teeth, once the dental plaque on the teeth has reacted with the enzyme, the enzyme would turn pink to allow the distribution of the dental plaque to be known. However, the method requires the coating of an enzyme on teeth, and the accompanying technical issues are quite inconvenient.

Although some instrument manufacturers have provided optical dental detection instruments for examining teeth, said instruments have been plagued by the technical problem of being incapable of differentiating between dental plaques and dental calculi. In addition, said instruments are also incapable of effectively identifying subgingival calculi. Also, said instruments require a detection operator to firstly find a fluorescent spot before an effective identification can be made, which makes analysis and processing even slower, and since a detection operator is required, the technical problem of being heavily reliant on the operation experience of the detection operator is also present. On the other hand, some instruments cannot automatically and directly photograph all of the teeth, and therefore a panoramic dental detection image is difficult to obtain.

SUMMARY OF THE INVENTION

Based on at least one object of the present invention, the present invention provides a dental photography or detection device, the dental photography or detection device comprises a housing, a multiphoton lens module, a rotation motor, an optical characteristic measurement module and an integrated circuit. The housing has an imaging end, and a handheld end opposite to the imaging end. The multiphoton lens module is disposed at the imaging end of the housing, and comprises a first filter and a first light source which are exposed on the surface of the multiphoton lens module. The rotation motor is connected to the housing and the multiphoton lens module and used for rotating according to a rotation control signal, so as to drive the multiphoton lens module to rotate. The optical characteristic measurement module is disposed on the housing and comprises an image sensor, used for receiving a first detection light resulted from a light passing through the first filter after being reflected or excited by the first light source illuminating on at least a tooth and gums thereof, and then generating at least one dental detection image corresponding to at least one tooth accordingly. The integrated circuit is disposed on the housing and electrically connected to the optical characteristic measurement module and the rotation motor, used for receiving a dental detection image and generating the rotation control signal.

According to the above-mentioned dental photography or detection device, the multiphoton lens module further comprises a second filter and a second light source which are exposed on the surface of the multiphoton lens module, the image sensor further receives a second detection light resulted from a light passing through the second filter after being reflected or excited by the second light source illuminating on at least a tooth and gums thereof, and the optical characteristic measurement module generates at least one dental detection image corresponding to at least one tooth according to the first detection light and the second detection light.

According to the above-mentioned dental photography or detection device, the multiphoton lens module further comprises a third light source and a condenser which are exposed on the surface of the multiphoton lens module, and the optical characteristic measurement module further comprises a spectroscope and further receives a third detection light resulted from a light reflected or excited to the condenser by the third light source illuminating on at least a tooth and gums thereof.

According to the above-mentioned dental photography or detection device, the dental photography or detection device further comprises a fiber optic component, and the fiber optic component is disposed on the housing and used for being connected to the multiphoton lens module and the optical characteristic measurement module, so as to transmit the first detection light, the second detection light and the third detection light.

According to the above-mentioned dental photography or detection device, the first light source comprises a plurality of first light emitting diodes, the second light source comprises a plurality of second light emitting diodes, in which a first band of a first light emitted by the first light emitting diodes is different from a second band of a second light emitted by the second light emitting diodes, a first optical pass band of the first filter is different from a second optical pass band of the second filter, and the third light source comprises a plurality of halogen lamps.

According to the above-mentioned dental photography or detection device, both the first light and the second light are lights in a range from a UV (Ultraviolet)-radiation B band to a green light band.

According to the above-mentioned dental photography or detection device, and the dental photography or detection device further comprises a display screen. The display screen is disposed outside of the housing and electrically connected to the integrated circuit, and used for displaying an analyzed and processed dental detection image, wherein the integrated circuit is used for analyzing and processing a dental detection image, and/or the integrated circuit is used for transmitting a dental detection image to an external device in a wired or wireless communication mode, after a plurality of dental detection images have in been analyzed and processed, a panoramic dental detection image showing all the teeth in an oral cavity is obtained, the analyzed and processed dental detection images are displayed on the display screen, and the displayed dental detection images at least includes a dental, dental plaque distribution, subgingival calculus distribution and dental calculus distribution corresponding to a tooth.

According to the above-mentioned dental photography or detection device, the dental photography or detection device further comprises a switch switching component, the switch switching component is disposed on the housing and electrically connected to the integrated circuit, and used for enabling a detection operator to switch between a power switch and/or an operation mode of the dental photography or detection device.

Based on at least one object of the present invention, the present invention provides a dental image detection system, and the dental image detection system comprises the above-mentioned dental photography or detection device and a cloud server. The cloud server is communicatively connected to the dental photography or detection device, and used for receiving, recording, analyzing and processing dental detection images.

According to the above-mentioned dental image detection system, and the dental image detection system further comprises an electronic device. The electronic device is communicatively connected to the cloud server, and used for receiving dental health analysis reports corresponding to dental detection images transmitted by the cloud server.

In other words, the dental photography or detection device of the present invention is capable of automatically photographing a panoramic dental detection image, obtaining dental detection images formed by detection lights corresponding to different light sources, and finding out dental plaque distribution, dental calculus distribution and subgingival calculus distribution of teeth from the dental detection images. All the detection, analysis and processing are automatically completed, which not only provides the beneficial technical effect of fast and convenient detections, but also further provides dental health analysis reports corresponding to the dental detection images, enabling a subject or doctor to take corresponding actions according to the dental health analysis reports.

To enable a further understanding of said objectives, structures, characteristics, and effects, as well as the technology and methods used in the present invention and effects achieved, a brief description of the drawings is provided below followed by a detailed description of the preferred embodiments.

BRIEF DESCRIPTION OF THE DRAWINGS

The following diagrams are provided to facilitate better understanding of the present invention by a person of ordinary skill in the art, which are combined with the description of the present invention and constitute a part thereof. The figures show the illustrative embodiments of the present invention, and are provided for explaining the principle of the present invention together with the description of the present invention. The figures of the present invention include.

DETAILED DESCRIPTION OF THE PREFERRED EMBODIMENTS

To facilitate better understanding of the technical features, contents, advantages of the present invention and effects achieved thereby by the examiner. The present invention will be further described below in conjunction with the accompanying drawings and embodiments thereof. It should be understood that these drawings are only illustrative and supplementary to the description, and are not necessarily the true proportions and accurate configurations of implementations of the present invention, and therefore should not be restricted to the proportion and configuration relationship in the accompanying drawings, or considered as limiting the scope of protection of the present application.

Figure 1:
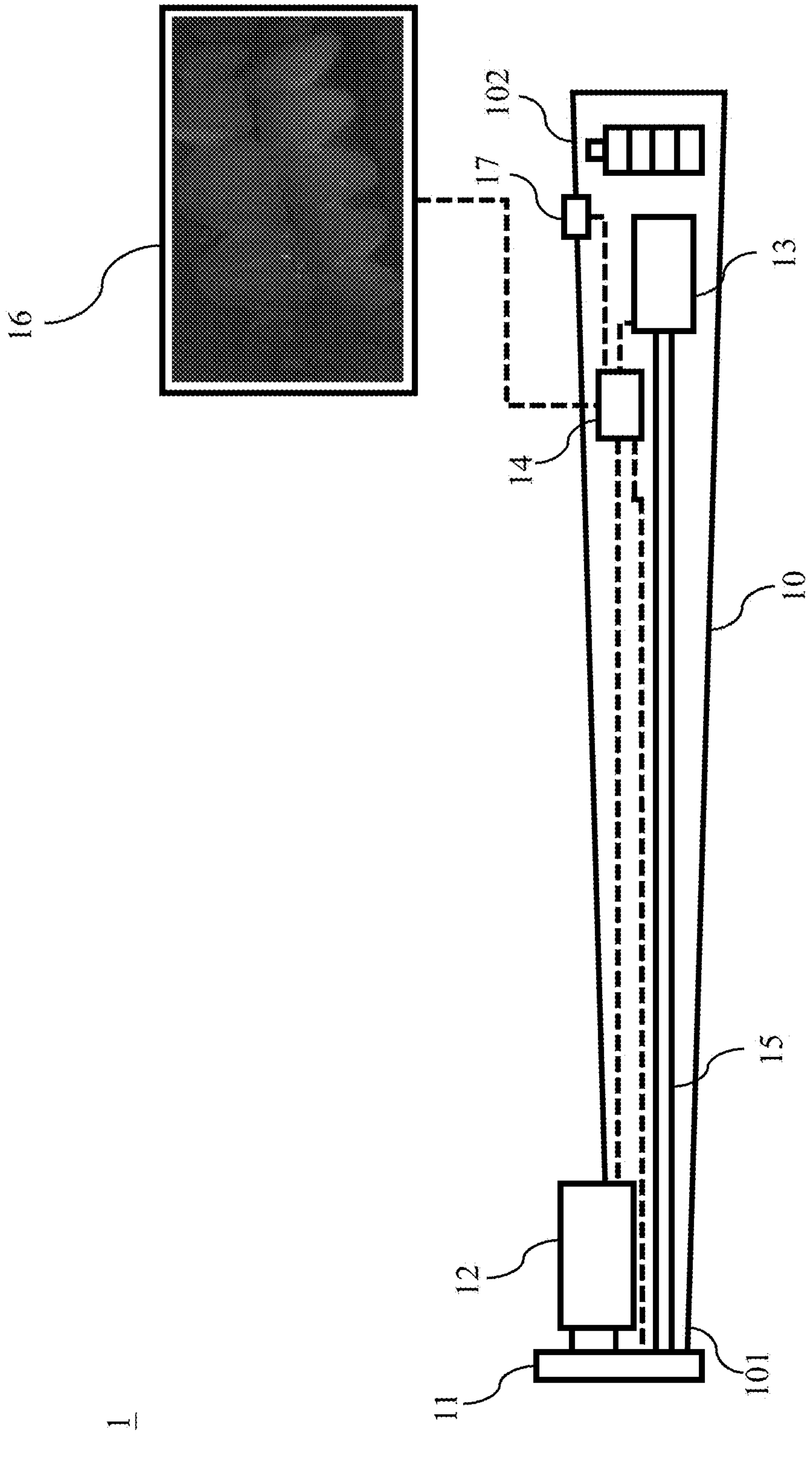
FIG. 1 is a dissected perspective view of a dental photography or detection device in accordance with an embodiment of the present invention.
Figure 2:
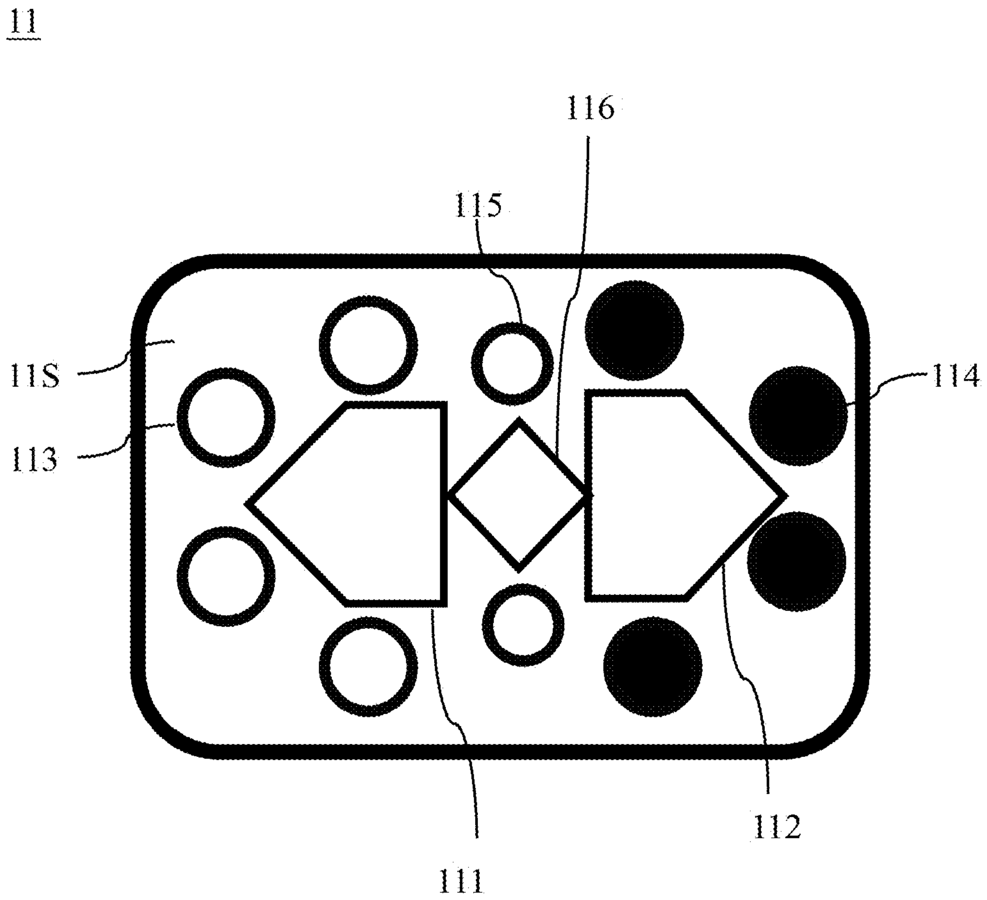
FIG. 2 is a front view of a multiphoton lens module of a dental photography or detection device in accordance with an embodiment of the present invention.

Refer to FIG. 1 and FIG. 2, FIG. 1 is a dissected perspective view of a dental photography or detection device in accordance with an embodiment of the present invention, and FIG. 2 is a front view of a multiphoton lens module of a dental photography or detection device in accordance with an embodiment of the present invention. A dental photography or detection device 1 comprises a housing 10, a multiphoton lens module 11, a rotation motor 12, an optical characteristic measurement module 13 and an integrated circuit 14. The housing 10 has an imaging end 101, and a handheld end 102 opposite to the imaging end 101. The multiphoton lens module 11 is disposed at the imaging end 101 of the housing 10, a detection personnel such as a doctor, a nurse, a medical examiner, etc. holds the dental photography or detection device 1 by holding the handheld end 102, and moves the dental photography or detection device 1 to enable the imaging end 101 to be located in the mouth of a subject, so as to enable the multiphoton lens module 11 to illuminate the teeth and the gums and obtain a corresponding dental detection image.

The multiphoton lens module 11 comprises a first filter 111, a second filter 112, a first light source 113 and a second light source 114 which are exposed on a surface 11S of the multiphoton lens module 11. The first light source 113 comprises a plurality of first light emitting diodes, the second light source 114 comprises a plurality of second light emitting diodes, in which a first band of a first light emitted by the first light emitting diodes is different from a second band of a second light emitted by the second light emitting diodes, and a first optical pass band of the first filter 111 is different from a second optical pass band of the second filter 112. Further, the plurality of first light emitting diodes are disposed on the left of the surface 11S of the multiphoton lens module 11, surroundingly provided in the perimeter of the first filter 111, and the plurality of second light emitting diodes are disposed on the right of the surface 11S of the multiphoton lens module 11, surroundingly provided in the perimeter of the second filter 112, but the present invention is not limited thereto. In addition, the first light emitted by the first light emitting diodes and the second light emitted by the second light emitting diodes are in a range from a UV (Ultraviolet)-radiation B band to a green light band.

The rotation motor 12 is connected to the housing 10 and the multiphoton lens module 11, and used for rotating according to a rotation control signal, so as to drive the multiphoton lens module 11 to rotate. The rotation motor 12 can be designed to be manually controlled or automatically controlled. By means of the rotation motor 12, the multiphoton lens module 11 is enabled to be rotated, so as to photograph dental detection images of different teeth, and a plurality of dental detection images of multiple different teeth can be further analyzed and processed (by means of the integrated circuit 14 or an external cloud server), in order to obtain a panoramic dental detection image of all the teeth in an oral cavity. In other words, by means of the rotation motor 12, the dental photography or detection device 1 provided by the present invention can sequentially photograph all the teeth, so as to obtain a panoramic dental detection image.

The optical characteristic measurement module 13 is disposed on the housing 10 and comprises an image sensor, used for receiving a first detection light resulted from a light passing through the first filter 111 after being reflected or excited by the first light source 113 illuminating on at least a tooth and gums thereof, as well as a second detection light resulted from a light passing through the second filter 112 after being reflected or excited by the second light source 114 illuminating on at least a tooth and gums thereof, and then generating at least one dental detection image corresponding to at least one tooth accordingly. The image sensor may be a camera capable of sensing lights of near infrared or visible light bands. In other words, after the first detection light and the second detection light are received by the image sensor, a corresponding dental detection image can be generated according to the first detection light and the second detection light. Selectively, in other embodiments, the second filter 112 and the second light source 114 may be elements which are selectively disposed, and are not essential elements. Meanwhile, the image sensor receives the first detection light to generate at least one dental detection image corresponding to at least one tooth.

The integrated circuit 14 is disposed on the housing 10 and electrically connected to the optical characteristic measurement module 13, the rotation motor 12 and the first light source 113 and the second light source 114 of the multiphoton lens module 11, and used for receiving a dental detection image and generating the rotation control signal. Further, the integrated circuit 14 is used for analyzing and processing dental detection images, and/or the integrated circuit 14 is used for transmitting a dental detection image to an external device in a wired or wireless communication mode, the external device is a cloud server, and the cloud server can be used for analyzing and processing the dental detection image.

Figure 3:
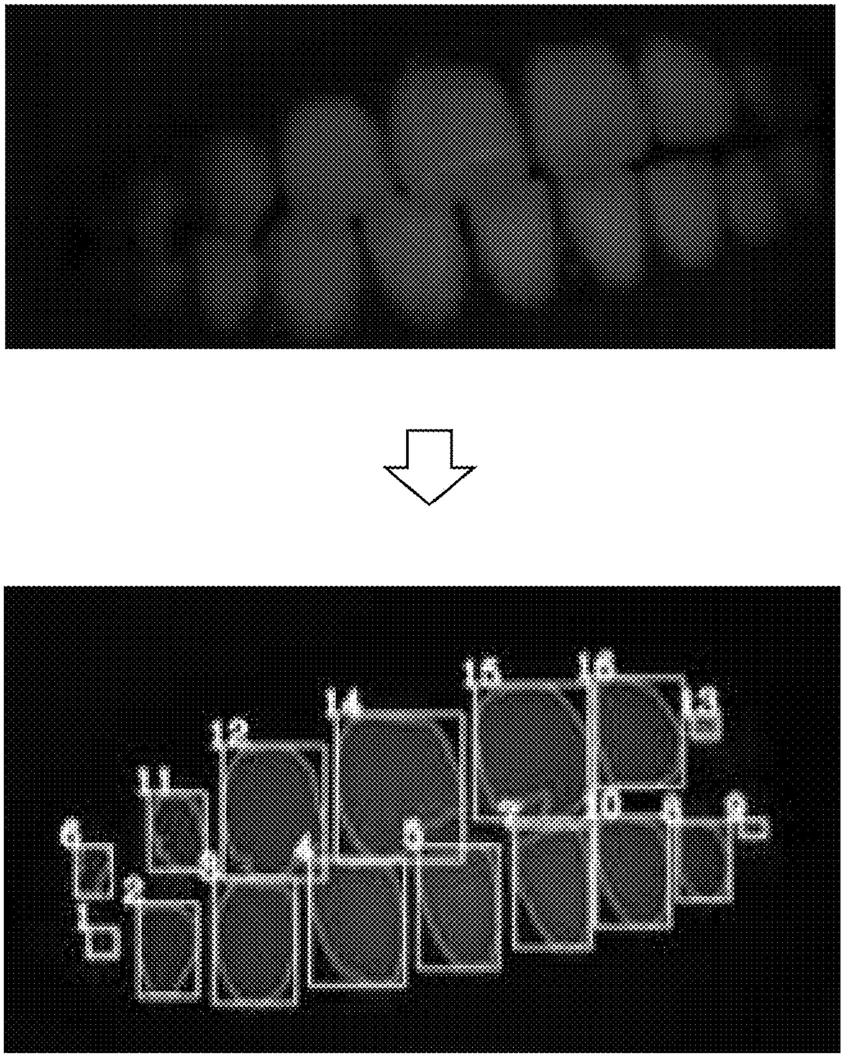
FIG. 3 is a view of a dental obtained by a dental photography or detection device after acquiring, analyzing and processing a dental detection image in accordance with an embodiment of the present invention.

For instance, the integrated circuit 14 can be a processing unit having a greater computational power, and has a recognition model of artificial intelligence algorithm (for example, a model based on convolutional neural network), and therefore is capable of analyzing and processing dental detection images. Refer to FIGS. 1-3, after the dental detection image in the upper part of FIG. 3 is analyzed and processed, the dental of the teeth is marked and shown in the lower part of FIG. 3.

In addition, apart from the dental, the dental detection image also includes dental plaques, dental calculi and subgingival calculi, but if only an image sensor is used for imaging, the differences between dental plaques, dental calculi and subgingival calculi cannot be differentiated effectively. That is, only tartars are recognized, but it cannot be known whether the tartars are dental plaques, dental calculi or subgingival calculi.

In order to solve the above-mentioned technical problems, preferably, the multiphoton lens module 11 further comprises a third light source 115 and a condenser 116 which are exposed on the surface 11S of the multiphoton lens module 11, and the optical characteristic measurement module 13 further comprises a spectroscope and further receives a third detection light resulted from a light reflected to the condenser 116 by the third light source 115 illuminating on at least a tooth, in which the third light source 115 comprises a plurality of halogen lamps, and the plurality of halogen lamps are disposed near the condenser 116. In an embodiment of the present invention, when only the first filter 111 and the first light source 113 are available, fluorescent images of dental calculi (on the dental or subgingival) are identical and cannot be differentiated therebetween, therefore, preferably, the second filter 112 and the second light source 114 are recommended to be provided. Preferably, it is further recommended that the third light source 115 and the condenser 116 are also provided.

Moreover, the spectroscope receives the first detection light, the second detection light and the third detection light to obtain a spectrum of tartars. By analyzing and processing the spectrum by means of the integrated circuit 14, it can be known whether the tartars are dental plaques, dental calculi or subgingival calculi.

Figure 4:
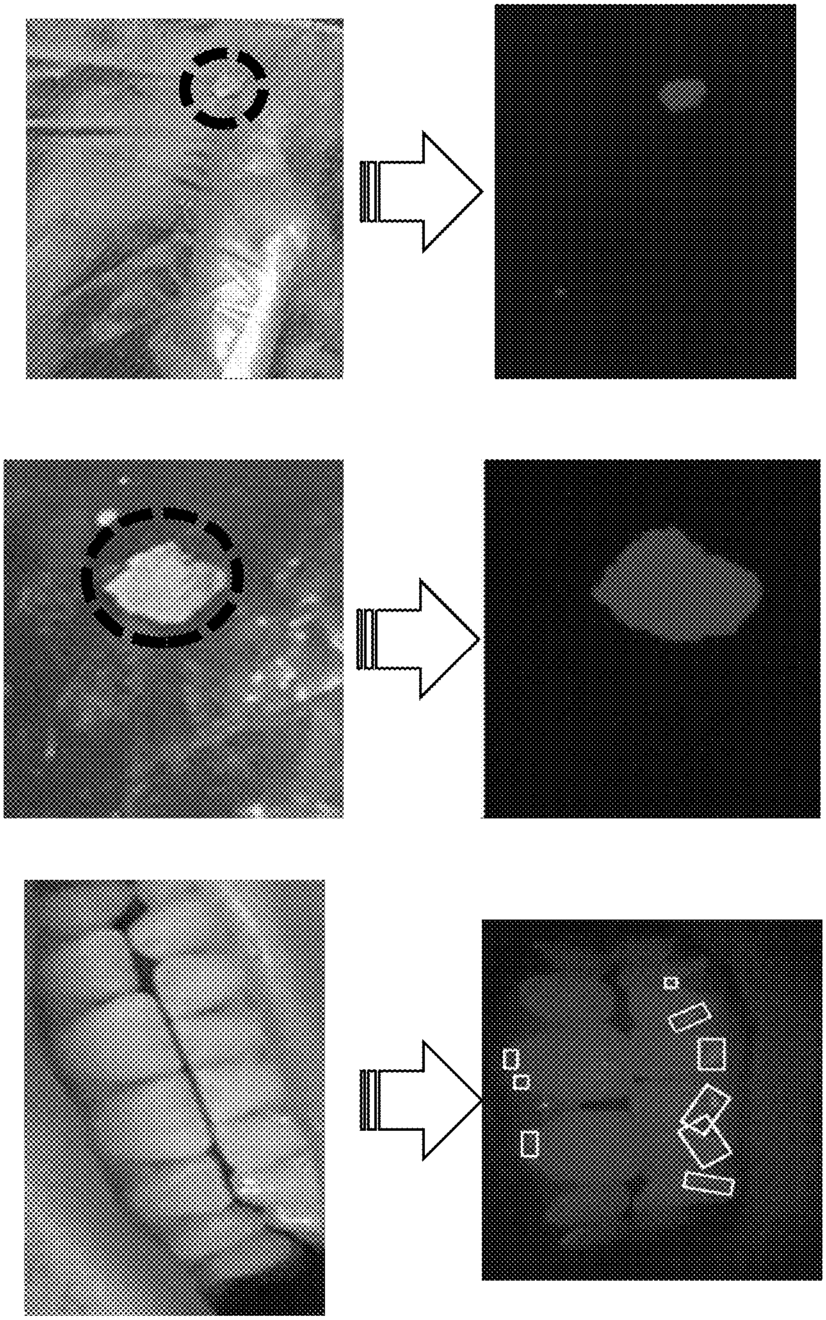
FIG. 4 are dental detection images acquired, analyzed and processed by a dental photography or detection device in accordance with an embodiment of the present invention, in which the dental detection images can be used for multiple calculation and analysis, so as to find out distribution of dental plaques or distribution of dental calculi on the dental.

Refer to FIGS. 1, 2 and 4, in which FIG. 4 shows dental detection images, which can be used for multiple calculation and analysis, so as to find out distribution of dental plaques or distribution of dental calculi on the dental. The upper part of FIG. 4 shows images from a camera in general, while the lower part thereof shows images of excitation under the first light source 113, and the white boxes in the lower left part of the image are white identification boxes added after being analyzed by the integrated circuit 14. The middle lower part and the lower right part respectively show images of dental calculi on an in vitro dental and subgingival in excitation under the first light source 113, which are the same as the color of excitation in the image in the lower left part, and therefore the optical characteristic measurement module 13 or other light sources apart from the images are required for further analyzing differences between the tartars (dental plaques, dental calculi on the dental, subgingival calculi). In simple words, when only the first filter 111 and the first light source 113 are available, fluorescent images of dental calculi (on the dental or subgingival) are identical and cannot be differentiated therebetween, therefore, preferably, the second filter 112 and the second light source 114 are recommended to be provided. Preferably, it is further recommended that the third light source 115 and the condenser 116 are also provided.

Further refer to FIGS. 1 and 2, the dental photography or detection device 1 further comprises a fiber optic component 15, and the fiber optic component 15 is disposed on the housing 10 and used for being connected to the multiphoton lens module 11 and the optical characteristic measurement module 13, so as to transmit the first detection light, the second detection light and the third detection light. In other embodiments, the fiber optic component 15 may also be replaced by using optical waveguides of other types.

In an embodiment of the present invention, the dental photography or detection device 1 may further comprise a display screen 16. The display screen 16 is disposed outside of the housing 10 and electrically connected to the integrated circuit 14, and used for displaying an analyzed and processed dental detection image, wherein the displayed dental detection image at least includes a dental, dental plaque distribution, subgingival calculus distribution and dental calculus distribution corresponding to a tooth.

In addition, the dental photography or detection device 1 further comprises a switch switching component 17, the switch switching component 17 is disposed on the housing 10 and electrically connected to the integrated circuit 14, and used for enabling a detection operator to switch between a power switch and/or an operation mode of the dental photography or detection device 1.

Figure 5:
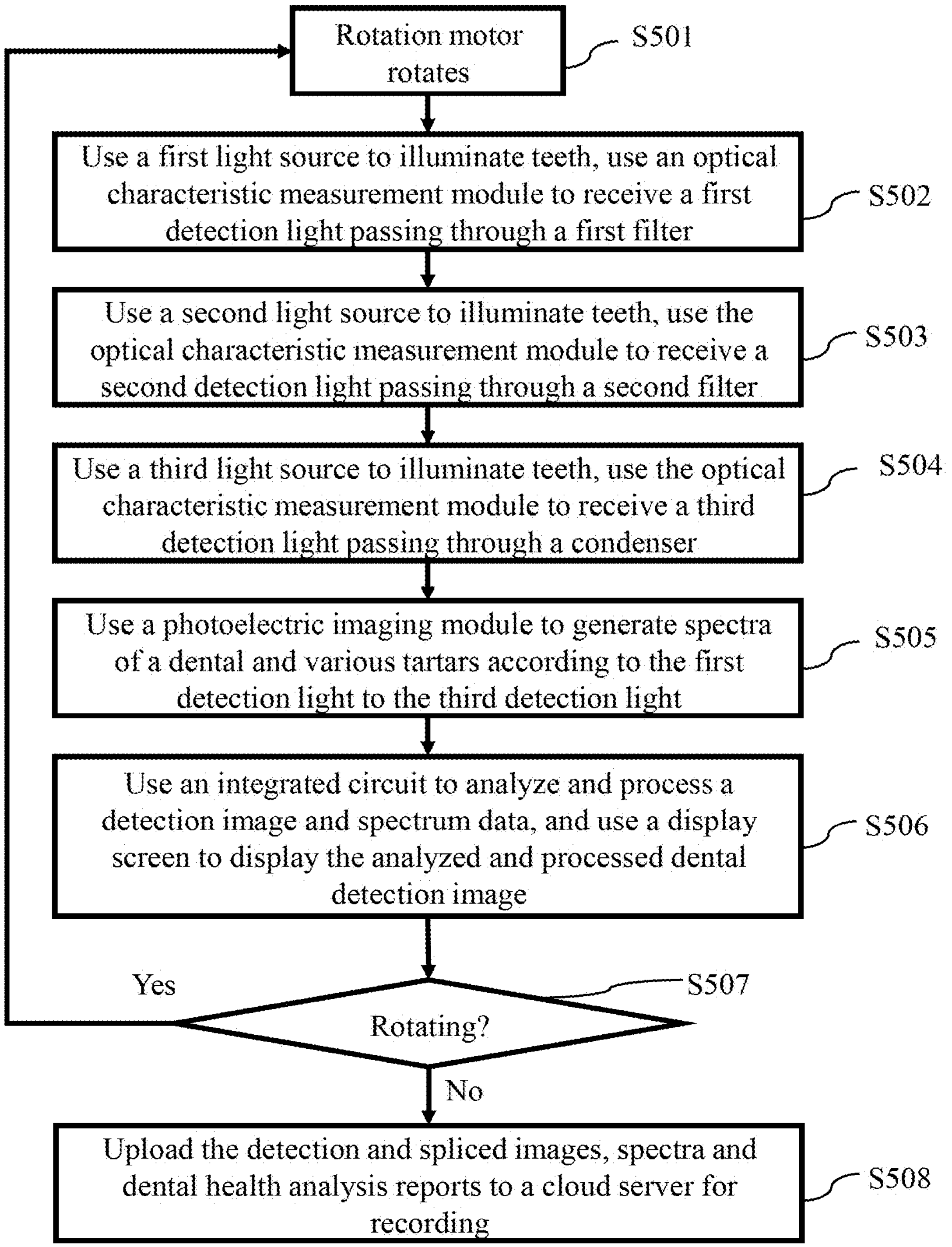
FIG. 5 is a flow chart of a dental image detection method in accordance with an embodiment of the present invention.

Refer to FIGS. 1, 2 and 5, in which FIG. 5 is a flow chart of a dental image detection method in accordance with an embodiment of the present invention. As indicated in FIG. 5, firstly in step S501, the rotation motor 12 rotates, so as to rotate the multiphoton lens module 11 to a specific angle. Next, in step S502, the first light source 113 is used to illuminate teeth, and the optical characteristic measurement module 13 is used to receive the first detection light passing through the first filter 111. Next, in step S503, the second light source 114 is used to illuminate teeth, and the optical characteristic measurement module 13 is used to receive the second detection light passing through the second filter 112. Next, in step S504, the third light source 115 is used to illuminate teeth, and the optical characteristic measurement module 13 is used to receive a third detection light passing through the condenser 116. It should be noted here that steps S502 and S503 are not the essential steps, and may be removed in other embodiments.

Subsequently, in step S505, the optical characteristic measurement module 13 is used to generate a dental image and spectra of various tartars according to the first detection light to the third detection light. Next, in step S506, the integrated circuit 14 is used to analyze and process the detection image and spectrum data, and the display screen 16 is used to display the analyzed and processed dental detection image. In addition, by analyzing and processing the detection images and spectra of various tartars, the analyzed and processed dental detection images displayed by the display screen 16 include a dental, dental plaque distribution, dental calculus distribution and subgingival calculus distribution.

Subsequently, in step S507, it is determined that whether another rotation of the rotation motor 12 is required, so as to further obtain other dental images and tartar spectra. If another rotation of the rotation motor 12 is required, step S501 is executed; otherwise, step S508 is executed. In step S508, the detection and spliced images, spectra and dental health analysis reports are uploaded to the cloud server for recording. It should be noted that the embodiment of the above-mentioned method is implemented on the basis that the integrated circuit 14 has sufficient computational power, and if the computational power of the integrated circuit 14 is insufficient, in step S506, the integrated circuit 14 may transmit the detection images and spectra of various tartars to the cloud server, such that the cloud server performs the analysis and processing.

Figure 6:
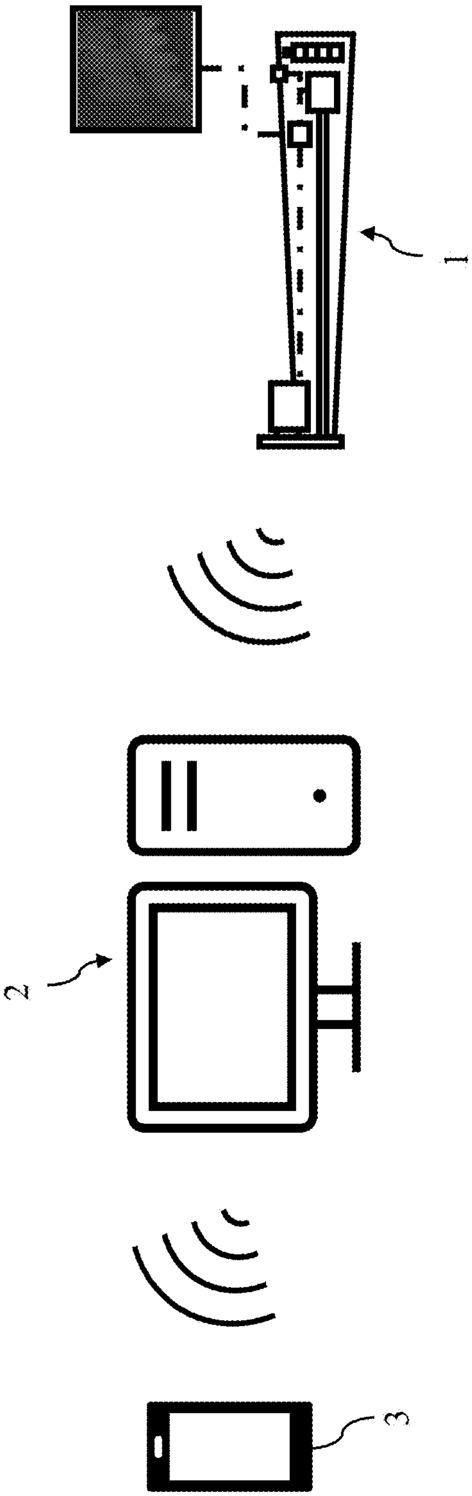
FIG. 6 is a view of a dental image detection system in accordance with an embodiment of the present invention.

Refer to FIG. 6, which is a view of a dental image detection system in accordance with an embodiment of the present invention. The present invention further provides a dental image detection system, and the dental image detection system comprises the above-mentioned dental photography or detection device 1, a cloud server 2 and an electronic device 3 of a subject. The cloud server 2 is communicatively connected to the dental photography or detection device 1, and used for receiving, recording, analyzing and processing dental detection images and tartar spectra. The electronic device 3 is communicatively connected to the cloud server 2, and used for receiving dental health analysis reports corresponding to the dental detection images transmitted by the cloud server 2.

From the above description, it can be known that the dental photography or detection device of the present invention rotates a multiphoton lens module by means of a rotation motor, so as to automatically photograph a panoramic dental detection image, and uses an optical characteristic measurement module to construct a dental detection image according to multiple detection lights obtained by the multiphoton lens module, and uses an integrated circuit and/or a cloud server to analyze and process the dental detection image, in which the analyzed and processed dental detection image includes the dental plaque distribution, the dental calculus distribution and subgingival calculus distribution in teeth. Accordingly, the dental photography or detection device has the technical effects of convenient and accurate detection, in conjunction with artificial intelligence, a dental health analysis report corresponding to the dental detection image can be provided to the subject or doctor, so as to enable the subject or doctor to take corresponding medical actions or health care actions.

It should be understood that the above-mentioned embodiments are merely for illustrating the technical ideas and characteristics of the present invention, the purpose thereof is to allow a person of ordinary skill in the art to understand the content of the present invention and make implementations accordingly, and are not to be used to limit the scope of the present invention. Any simple changes and modifications which are effectually equivalent and made according to the spirit disclosed in the present invention still fall within the scope of the claims of the present invention.

What is claimed is:

1. A dental photography or detection device, comprising:

a housing having an imaging end and a handheld end opposite to the imaging end;

a multiphoton lens module disposed at the imaging end of the housing, comprising a first filter and a first light source which are exposed on a surface of the multiphoton lens module;

a rotation motor connected to the housing and the multiphoton lens module, used for rotating according to a rotation control signal, thereby driving the multiphoton lens module to rotate;

an optical characteristic measurement module disposed on the housing, comprising an image sensor, used for receiving a first detection light resulted from a light passing through the first filter after being reflected or excited by the first light source illuminating on at least a tooth and gums thereof, and then generating at least one dental detection image corresponding to at least one tooth accordingly; and an integrated circuit disposed on the housing and electrically connected to the optical characteristic measurement module and the rotation motor, used for receiving the dental detection image and generating the rotation control signal;

wherein the multiphoton lens module further comprises a second filter and a second light source which are exposed on the surface of the multiphoton lens module, the image sensor further receives a second detection light resulted from a light passing through the second filter after being reflected or excited by the second light source illuminating on at least a tooth and gums thereof, and the optical characteristic measurement module generates at least one dental detection image corresponding to at least one tooth according to the first detection image and the second detection image.

2. The dental photography or detection device according to claim 1, wherein the multiphoton lens module further comprises a third light source and a condenser which are exposed on the surface of the multiphoton lens module, and the optical characteristic measurement module further comprises a spectroscope and further receives a third detection light resulted from a light reflected or excited to the condenser by the third light source illuminating on at least a tooth and gums thereof.

3. The dental photography or detection device according to claim 2, further comprising:

a fiber optic component disposed on the housing, used for being connected to the multiphoton lens module and the optical characteristic measurement module, thereby transmitting the first detection light, the second detection light and the third detection light.

4. The dental photography or detection device according to claim 3, wherein the first light source comprises a plurality of first light emitting diodes, the second light source comprises a plurality of second light emitting diodes, a first band of a first light emitted by the first light emitting diodes is different from a second band of a second light emitted by the second light emitting diodes, a first optical pass band of the first filter is different from a second optical pass band of the second filter, and the third light source comprises a plurality of halogen lamps.

5. The dental photography or detection device according to claim 4, wherein the first light and the second light are lights in a range from a UV (Ultraviolet)-radiation B band to a green light band.

6. The dental photography or detection device according to claim 5, further comprising:

a display screen disposed outside of the housing and electrically connected to the integrated circuit, used for displaying the analyzed and processed dental detection image, wherein the integrated circuit is used for analyzing and processing the dental detection image, and/or the integrated circuit is used for transmitting the dental detection image to an external device for analyzing and processing in a wired or wireless communication mode, after a plurality of dental detection images have been analyzed and processed, a panoramic dental detection image showing all the teeth in an oral cavity is obtained, the analyzed and processed dental detection image is displayed on the display screen, and the displayed dental detection image at least includes a dental, a dental plaque distribution, a subgingival calculus distribution and a dental calculus distribution corresponding to the teeth.

7. The dental photography or detection device according to claim 4, further comprising:

a switch switching component disposed on the housing and electrically connected to the integrated circuit, used for enabling a detection operator to switch between a power switch and/or an operation mode of the dental photography or detection device.

8. A dental image detection system, comprising:

the dental photography or detection device according to claim 1; and a cloud server communicatively connected to the dental photography or detection device, used for receiving, recording, analyzing and processing dental detection images.

9. The dental image detection system according to claim 8, further comprising:

an electronic device communicatively connected to the cloud server, used for receiving a dental health analysis report corresponding to the dental detection images transmitted by the cloud server.

* * * * *